United States Patent [19]

Angell

[11] 4,042,979
[45] Aug. 23, 1977

[54] VALVULOPLASTY RING AND PROSTHETIC METHOD

[76] Inventor: William W. Angell, 19174 De Haviland, San Jose, Calif. 95070

[21] Appl. No.: 704,542

[22] Filed: July 12, 1976

[51] Int. Cl.² .............................................. A61F 1/22
[52] U.S. Cl. ...................................................... 3/1.5
[58] Field of Search ........................ 3/1.5; 128/334 R

[56] References Cited
U.S. PATENT DOCUMENTS

| 3,371,352 | 3/1968 | Siposs et al. | 3/1.5 |
| 3,656,185 | 4/1972 | Carpentier | 3/1.5 |

Primary Examiner—Ronald L. Frinks
Attorney, Agent, or Firm—Thomas E. Ciotti

[57] ABSTRACT

An adjustable valvuloplasty ring that comprises a C-shaped frame that is sized and shaped to extend about the circumference of the left atrioventricular orifice along the base of the anterior cusp of the mitral valve; an expandable sleeve connected to the frame that together therewith forms a closed annulus, the sleeve being adapted to extend about the remainder of the circumference of the orifice; and a drawstring running through the sleeve by which the sleeve may be contracted to constrict and remodel the orifice and secured in place to maintain such constriction.

13 Claims, 6 Drawing Figures

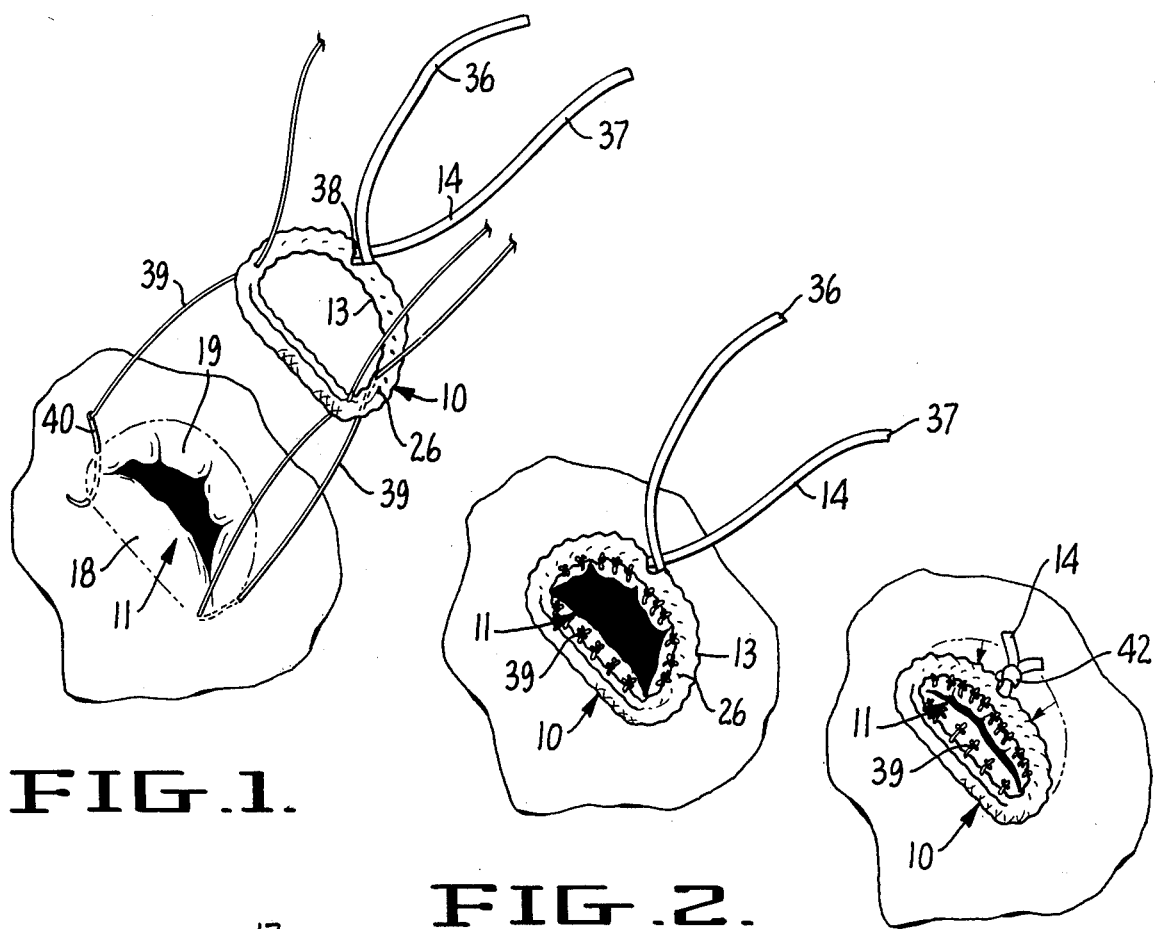
FIG. 1.
FIG. 2.
FIG. 3.
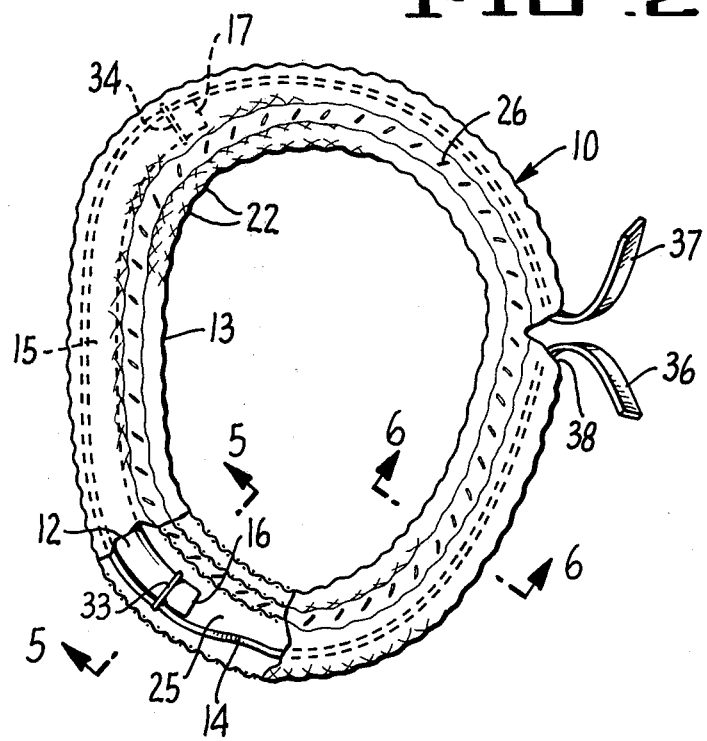
FIG. 4.
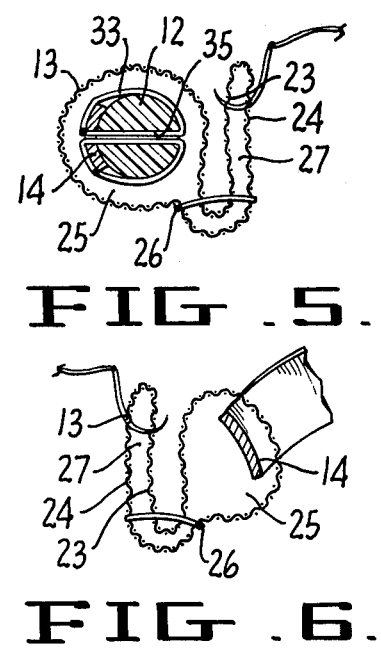
FIG. 5.
FIG. 6.

VALVULOPLASTY RING AND PROSTHETIC METHOD

BACKGROUND OF THE INVENTION

1. Field of the Invention

The invention is a valvuloplasty ring and a surgical method for constricting and remodeling the orifice of an atrioventricular orifice.

2. Description of Prior Art

U.S. Pat. No. 3,656,185 reviews the prostheses and techniques that are available for providing annular support for atrioventricular orifices. The valvuloplasty ring that is the subject of this patent consists of a rigid, channeled, reniformshaped frame, a stitchable cord that fits in the frame channel, and a filament that holds the cord in the channel. The frame-cord-filament assembly is covered by a fabric sheath. This ring is sutured in place about the periphery of the orifice using the cord as a sewing flap with the flat portion of the frame lying along the base of the large cusp. Since this ring is rigid over its entire circumference, it has a substantially fixed annular-size to which the orifice conforms once it is sutured in place. This ring must be sized precisely prior to its implantation.

It is also believed that a surgical procedure, called the "De Vega annuloplasty", for repairing enlarged cardiac orifices has been practiced in Europe that involves lacing a thread through the tissue about the periphery of the orifice, pulling the ends of the thread together to constrict the orifice, and then tying the thread ends in place. However, this procedure is done only on the low pressure tricuspid valve side of the heart.

SUMMARY OF THE INVENTION

The invention is a valvuloplasty ring for an atrioventricular orifice comprising: a frame that is sized and shaped to extend about a significant portion of the circumference of the orifice; an expandable member extending from the ends of the frame that is sized and shaped to extend about at least a substantial portion of the remainder of the circumference of the orifice; means for affixing the ring about the circumference of the orifice; and means for expanding and contracting the expandable member whereby the size of the ring and orifice may be adjusted after implantation.

The invention also encompasses a method for constricting and remodeling an atrioventricular orifice comprising: affixing a noncontractile support member about a significant portion of the circumference of the orifice, normally that portion that is naturally fixed and cannot be constricted; affixing a contractile support member that is attached to the rigid support member about at least a substantial portion of the remainder of the circumference of said orifice; contracting the contractile support member to a contracted position, whereby the orifice is constricted; and fixing the contractile support member in said contracted position.

Preferably, in both the ring and method the expandable (contractile) member extends about the entire remainder of the orifice circumference.

BRIEF DESCRIPTION OF THE DRAWINGS

In the drawings:

FIG. 1 is a dimetric view of the preferred embodiment of the valvuloplasty ring of the invention and a mitral valve before the ring is placed in position about the left atrioventricular orifice;

FIG. 2 is a dimetric view of the valvuloplasty ring and mitral valve of FIG. 1 with the ring sutured in place about the orifice;

FIG. 3 is a dimetric view of the valvuloplasty ring and mitral valve of FIG. 1 with the ring sutured in place about the orifice and contracted to make the orifice smaller;

FIG 4 is an enlarged, top plan view of the valvuloplasty ring of FIG. 1 partly cut away;

FIG. 5 is an enlarged sectional view taken along line 5—5 of FIG. 4; and

FIG. 6 is an enlarged sectional view taken along line 6—6 of FIG. 4.

DESCRIPTION OF THE PREFERRED EMBODIMENT

The preferred embodiment of the valvuloplasty ring is generally designated 10 in the drawings, and the mitral valve about which it is used is generally designated 11. The materials used to make ring 10 should be medical grade and biocompatible. Within these prescriptions a great variety of polymeric and metallic materials may be used. Referring to FIGS. 4–6, ring 10 is basically composed of three elements: a frame 12, an elastic sleeve 13, and a drawstring 14.

Frame 12 is cylindrical and includes a flat middle segment 15 and a pair of arcuate end flanges 16, 17. Frame 12 may be rigid or flexible but is must not be constrictable. The shape of frame 12 resembles a letter "C" that has been spread open. As depicted in phantom in FIG. 1 the flat middle segment 15 is sized and shaped to lie longitudinally along the portion of the orifice of valve 11 that defines the base of the anterior cusp 18 thereof. That portion of the orifice is naturally fixed and cannot be constricted or remodeled significantly. The length and shape of frame 12 may vary depending upon the length of the anterior cusp annulus of the valve for which it is used. The end flanges 16, 17 are sized and shaped to extend generally to the commissures of the anterior cusp 18 of valve 11. Frame 12 is preferably made of a biocompatible polymer, such as Delrin polymer (a polyformaldehyde of greater than 15,000 molecular weight sold by DuPont).

Sleeve 13 is elastic; that is, it is expandable and contractable. It may be so because of its mechanical structure and/or its chemical composition. Preferably it is made from a knit fabric, such as Dacron polymer (polyethylene terephthalate) fabric, and has ribs 22 in it to facilitate its expansion and contraction. Sleeve 13 completely encloses frame 12 and extends outwardly from flanges 16, 17 to form a closed annulus of generally reniform shape. It is not necessary that sleeve 13 enclose frame 12 completely. Partial rings in which the sleeve merely extends from the frame ends without forming a closed annulus are feasible. The sleeve will however usually extend around greater than about 50% of the portion of the orifice not surrounded by frame 12.

As seen in FIGS. 5 and 6, sleeve 13 is composed of two layers of fabric: an inner layer 23, and an outer layer 24 that form a pocket 25 on the outer side of ring 10. Pocket 25 contains frame 12 and drawstring 14. A thread seam 26 through layers 23 and 24 closes pocket 25. Seam 26 is composed of a running stitch along frame 12 and an interrupted stitch between ribs 22 about the remainder of sleeve 13. The remaining (inner) portion 27 of sleeve 13 is held against the exterior of pocket 25 and acts as a sewing flange for sewing ring 10 about the valve orifice.

Referring again to FIG. 4, drawstring 14 extends completely about ring 10 within pocket 25. Preferably it is made from flat Teflon polymer (polytetrafluoroethylene) fabric tape. Drawstring 14 is tied to each end flange 16, 17 of frame 12 by threads 33, 34 that respectively extend through holes 35 (only one hole 35 is shown, FIG. 5) formed diametrically through end flanges 16, 17 and are wrapped circumferentially about flanges 16, 17 and drawstring 14. Drawstring 14 extends about the outer edge of frame 12 and its ends 36, 37 exit from pocket 25 via a hole 38 therein located generally opposite segment 15 of frame 12.

Ring 10 may be used to correct distortions of the normal anatomy of the orifice, correct dilation of the orifice, reposition displaced or incompetent cusps, remodel distended commissures, support the remaining annulus after resection of a portion or supplement the natural cusps to form an operative valve. FIGS. 1-3 illustrate its use in constricting the orifice of a mitral valve 11.

Referring to FIG. 1, ring 10, with sleeve 13 sized to fit about the left atrioventricular orifice at the base of valve 11, is placed about the circumference of the orifice in the atrial position with segment 15 lying longitudinally along the base of anterior cusp 18 (position shown in phantom). Segment 15 thus acts as a rigid support for that portion of the orifice. Correspondingly, the sleeve 13 of ring 10 fits about the remainder of the circumference of the orifice at the base of posterior cusp 19 and serves as a contractile support for such remainder. Ring 10 is affixed about the circumference of the orifice by a suture 39 sewn through inner portion 27 of sleeve 13 and the fibrous tissue ring that defines the orifice. This suturing may be done by conventional techniques using a hooked needle 40 (FIG. 1). FIG. 2 shows ring 10 sewn in place about the orifice with sleeve 13 in an expanded position. Ends 36, 37 of drawstring 14 are then gripped, crossed (FIG. 2) and pulled so as to contract sleeve 13 and thereby decrease the size of the orifice. Once the orifice has been constricted to the desired size (FIG. 3) sleeve 13 is fixed in its contracted state by tying the ends of drawstring 14 into a knot 42 or suturing the ends of the drawstring together. The excess segments of the ends of the drawstring 14 are then snipped off to complete the surgical placement of ring 10 about the orifice.

As will be appreciated, the size, and to some extent the annular shape, of ring 10 is adjustable by the manipulations of the expandable-contractable sleeve 13. Accordingly ring 10, or several sizes thereof, may be employed to correct deficiencies in cardiac valves of varying initial size, merely by expanding or contracting sleeve 13, as the case may be. Likewise, the surgeon may constrict the size of the valve orifice quickly and simply to the optimum or desired size by contracting sleeve 13 and tying it in place with drawstring 14. Selective constriction of the inferior or superior limb is also possible by merely pulling on one end of the drawstring 14. Ring 10 thus provides an improved means for accomplishing a superior repair or remodeling of defective orifices and/or valves. While the above described embodiment is tailored for use about the left atrioventricular embodiment is tailored for use about the left atrioventricular orifice, the ring may be easily adapted for use in correcting deficiencies of the right atrioventricular orifice and/or tricuspid valve. In such adaptations the ring will be sized larger to accommodate the correspondingly larger dimensions of the right atrioventricular orifice. Correspondingly, the frame of rings used for the right atrioventricular orifice will be sized and shaped to lie about at least the portion of the orifice lying along the base of the anterior cusp of the tricuspid valve.

Modifications of the above described embodiment of the valvuloplasty ring 10 and the valvuloplasty operation in which it is used that are obvious to those of skill in the medical art, surgical art, medical/surgical instrument art, or related arts are intended to be within the scope of the following claims.

I claim:

1. Adjustable valvuloplasty ring for an atrioventricular orifice comprising:
   a. a frame that is sized and shaped to extend about a significant portion of the circumference of the orifice;
   b. an expandable member extending from the ends of the frame that is sized and shaped to extend about at least a substantial portion of the remainder of the circumference of the orifice; and
   c. means for expanding and contracting the expandable member whereby the size of the ring and orifice may be adjusted.

2. The valvuloplasty ring of claim 1 including:
   d. means for affixing the ring about the circumference of the orifice.

3. The valvuloplasty ring of claim 1 wherein the expandable member is sized and shaped to extend about the entire remainder of the circumference of the orifice and thus together with the frame forms a closed annulus.

4. The valvuloplasty ring of claims 3 wherein the expandable member is a knit sleeve in which the frame is enclosed.

5. The valvuloplasty ring of claim 1 wherein the means for expanding and contracting the expandable member comprises a drawstring running through the expandable member.

6. The valvuloplasty ring of claim 4 wherein the means for expanding and contracting the knit sleeve is a drawstring that is attached to the frame, extends within the sleeve about the circumference of the ring, and exits from the sleeve via a hole therein.

7. The valvuloplasty ring of claim 1 wherein said significant portion is defined by the base of the anterior cusp and said substantial portion of the remainder is defined by the base of the posterior cusp.

8. The valvuloplasty ring of claim 1 wherein the atrioventricular orifice is the left atrioventricular orifice and the frame has a flat segment that is sized to lie longitudinally along the base of the anterior cusp of the mitral valve.

9. The valvuloplasty ring of claim 8 wherein the frame includes a pair of arcuate end flanges extending from the flat segment to the commissures of the anterior cusp of the mitral valve.

10. Method for constricting and remodeling an atrioventricular orifice comprising:
    a. affixing a noncontractile support member about a significant portion of the orifice;
    b. affixing a contractile support member that is attached to the noncontractile support member about at least a substantial portion of the remainder of the circumference of the orifice;
    c. contracting the contractile support member to a contracted position whereby the orifice is constricted; and d. fixing the contractile support member in said contracted position.

11. The method of claim 10 wherein the contracted support member is affixed about the entire remainder of the circumference of the orifice.

12. The method of claim 11 wherein said significant portion is defined by the base of the anterior cusp and said substantial portion of the remainder is defined by the base of the posterior cusp.

13. The method of claim 11 wherein the orifice is the left atrioventricular orifice and the rigid support member is affixed about the portion of the orifice circumference that lies along the base of the anterior cusp of the mitral valve.

* * * * *